(12) United States Patent
Ali et al.

(10) Patent No.: US 8,200,366 B2
(45) Date of Patent: Jun. 12, 2012

(54) METHOD AND SYSTEM FOR DETERMINING A VOLUME-BASED FILL PATTERN OF A MULTI-DOSE MEDICAMENT CONTAINER

(75) Inventors: Syed Y. Ali, Chicago, IL (US); Amy C. Biesenthal, Buffalo Grove, IL (US); Rishi Khullar, Deerfield, IL (US); Sean McGonagle, Buffalo Grove, IL (US); Greg Pankow, Morton Grove, IL (US)

(73) Assignee: Walgreen Co., Deerfield, IL (US)

( * ) Notice: Subject to any disclaimer, the term of this patent is extended or adjusted under 35 U.S.C. 154(b) by 913 days.

(21) Appl. No.: 12/187,218

(22) Filed: Aug. 6, 2008

(65) Prior Publication Data

US 2010/0031611 A1 Feb. 11, 2010

(51) Int. Cl.
*G07F 17/00* (2006.01)
*B65B 1/04* (2006.01)

(52) U.S. Cl. .......... 700/240; 700/239; 700/233; 53/473; 53/474; 53/237; 53/238; 53/168

(58) Field of Classification Search ................. 700/242, 700/233, 239, 240
See application file for complete search history.

(56) References Cited

U.S. PATENT DOCUMENTS

| | | | |
|---|---|---|---|
| 4,655,026 A | 4/1987 | Wigoda | |
| 4,998,623 A | 3/1991 | Doull | |
| 5,014,851 A * | 5/1991 | Wick | 206/539 |
| 5,450,710 A | 9/1995 | Jensen et al. | |
| 5,799,468 A * | 9/1998 | Eck et al. | 53/453 |
| 6,681,935 B1 * | 1/2004 | Lewis | 206/534 |
| 6,769,228 B1 | 8/2004 | Mahar | |
| 6,805,259 B2 | 10/2004 | Stevens et al. | |
| 7,100,793 B2 * | 9/2006 | Baum | 221/15 |
| 7,185,476 B1 | 3/2007 | Siegel et al. | |
| 7,426,814 B2 * | 9/2008 | Knoth | 53/473 |
| 7,712,288 B2 * | 5/2010 | Ramasubramanian et al. | 53/507 |
| 7,779,614 B1 * | 8/2010 | McGonagle et al. | 53/474 |
| 7,818,950 B1 * | 10/2010 | McGonagle et al. | 53/474 |
| 7,946,101 B1 * | 5/2011 | McGonagle et al. | 53/474 |
| 7,971,414 B1 * | 7/2011 | McGonagle et al. | 53/246 |

(Continued)

FOREIGN PATENT DOCUMENTS

DE 10 2006 007 136 A1 12/2006

(Continued)

OTHER PUBLICATIONS

"What is Medicine on Time?" <http://www.medicine-on-time.com/>, Medicine-On-Time University, 2008.

(Continued)

*Primary Examiner* — Michael K Collins
(74) *Attorney, Agent, or Firm* — Francis C. Kowalik; Marshall, Gerstein & Borun LLP; Randall G. Rueth

(57) ABSTRACT

A system and method for determining and communicating a volume-based fill pattern for a multi-dose medicament container is disclosed. Pill information corresponding to one or more pills for a patient to be packaged together may be obtained, and non-volume fill factors may be obtained. The volume-based fill pattern may be selected and indicated to be a cuboid volume or a packing parameter fill pattern. Pill and multi-dose medicament container data may be obtained and used to determine a fill pattern that is communicated to a filling entity for execution. The present disclosure may operate in accordance with multi-dose blister packs, and systems and methods of filling said blister packs.

10 Claims, 7 Drawing Sheets

U.S. PATENT DOCUMENTS

| | | |
|---|---|---|
| 2003/0216974 A1 | 11/2003 | Browne |
| 2004/0148054 A1* | 7/2004 | Schwartz .................. 700/231 |
| 2005/0004700 A1 | 1/2005 | DiMaggio |
| 2005/0033606 A1 | 2/2005 | Miller |
| 2005/0065645 A1 | 3/2005 | Liff et al. |
| 2005/0109658 A1* | 5/2005 | Bindford .................. 206/534 |
| 2005/0218152 A1 | 10/2005 | Simon |
| 2006/0074521 A1 | 4/2006 | Rice et al. |
| 2006/0149587 A1 | 7/2006 | Hill et al. |
| 2006/0161294 A1 | 7/2006 | DiMaggio |
| 2006/0161298 A1 | 7/2006 | DiMaggio |
| 2007/0067250 A1 | 3/2007 | Mahar |
| 2007/0095850 A1 | 5/2007 | Meyer |
| 2007/0112593 A1* | 5/2007 | Daya ........................... 705/2 |
| 2007/0185615 A1 | 8/2007 | Bossi et al. |
| 2007/0250346 A1 | 10/2007 | Luciano et al. |
| 2008/0071421 A1 | 3/2008 | Silverbrook et al. |
| 2008/0190076 A1* | 8/2008 | Klingel et al. .............. 53/493 |
| 2008/0265011 A1 | 10/2008 | Specker |
| 2009/0120042 A1* | 5/2009 | Zieher ......................... 53/467 |
| 2009/0250485 A1* | 10/2009 | Klingel ....................... 221/31 |

FOREIGN PATENT DOCUMENTS

| | | |
|---|---|---|
| EP | 1985544 A1 | 10/2008 |
| EP | 2112078 A1 | 10/2009 |

OTHER PUBLICATIONS

"Product Line" <http://www.medicine-on-time.com/>, Medicine-On-Time University, 2008.

"What is Medicine On Time," Medicine-On-Time University, 2008, 1 page.

"Product Line," Medicine-On-Time University, 2008, 5 pages.

International Search Report and Written Opinion for Application No. PCT/US09/033050 dated Apr. 15, 2009.

U.S. Appl. No. 12/102,570, filed Apr. 14, 2008.

U.S. Appl. No. 12/234,221, filed Sep. 19, 2008.

Office action for U.S. Appl. No. 12/102,570 issued Jan. 24, 2011.

Final Office action for U.S. Appl. No. 12/102,570 issued Jul. 25, 2011.

Office action for U.S. Appl. No. 12/234,221 issued Aug. 9, 2010.

Final Office action for U.S. Appl. No. 12/234,221 issued Jan. 27, 2011.

* cited by examiner

METHOD AND SYSTEM FOR DETERMINING A VOLUME-BASED FILL PATTERN OF A MULTI-DOSE MEDICAMENT CONTAINER

FIELD AND BACKGROUND OF THE DISCLOSURE

1. Field of the Disclosure

This disclosure relates generally to methods and systems for determining a fill pattern of multi-dose medicament containers for a plurality of prescriptions, nutraceuticals and/or over-the-counter medications.

2. Background Description

Traditional methods of packaging prescription medicaments include dispensing an entire single prescription's worth of the pills into a single medicament container affixed with a label displaying (among other data) patient identification, pill identification, dosage, and dosing regime instructions. If a patient needs to take multiple medications, a single, filled medicament container is typically issued for each prescription. Furthermore, if a patient is required to take the multiple medications at different times of the day and/or night, the patient must have all of the single, filled medicament containers readily available, and the patient must remember which and how many pill(s) needs to be taken when. Thus, traditional methods of packaging multiple prescription medicaments result in inconvenience to the patient as entire sets of single, filled medicament containers must be brought along. Other undesirable effects of traditional packaging methods include difficulty for the patient in remembering how many and what pill needs to be taken when, and whether or not the pill(s) have been ingested at the required time. These types of problems may lead to a patient failing to take a medicine at the appropriate time or taking too much medicine within a short period of time, which may cause adverse affects to patient health.

Recent advances in prescription packaging have attempted to mitigate these problems. For instance, a multi-dose blister pack may be used to fill one or more prescriptions for a patient. Examples of multi-dose blister packs may be found in U.S. Provisional Patent Application Ser. No. 60/947,169 entitled "Nested Multi-Dose Blister Pack," the entire disclosure of which is incorporated by reference. A machine and process for filling multi-dose blister packs may be found in U.S. Provisional Patent Application Ser. No. 60/940,790 entitled "Multi-Dose Filling Machine and Process," the entire disclosure of which is also incorporated by reference.

Multi-dose blister packs may contain a plurality of individual blister cells, each of which may hold one or more pills of different medications prescribed for a patient. One multi-dose blister pack, for instance, may be labeled "morning," so that each individual blister cell on the "morning" pack may contain the complete set of pills from a patient's one or more prescriptions that are to be ingested in the morning. The patient may also receive additional filled, multi-dose blister packs that have individual blister cells each containing the correct multiple medications to be ingested at "noon" and "night." Alternatively, blister packs may be filled to a different level of granularity. For example, a single multi-dose blister pack may have rows labeled "morning," "noon," and "night" and have columns labeled with the day of the week. So, on Tuesday night, the patient would ingest the correct set of pills from his/her one or more prescriptions by taking the pills from the individual blister cell located at the intersection of the "night" row and the "Tuesday" column. Of course, indicia of dosing regimes are not limited to the above examples and may use any indicia corresponding to a dosing regime. Other fill patterns of multi-dose blister packs are also possible.

Multi-dose blister packs may be perforated into individual, easily-portable blister cells. The blister cells on a single multi-dose blister pack may be similarly sized, or blister cells may be sized differently on a single multi-dose blister pack. Each blister cell may be labeled on the back to identify different medications contained within the blister cell, and may also list patient information, time/day/date information for ingestion and/or other dosing regime instructions, and the like. A patient may separate out from the pack the specific blister cells that s/he will need during a specific time period, and thus does not need to carry multiple large single filled medicament containers for each of his/her one or more prescriptions. The patient is not required to sort out the dosages of multiple medications for each medication's dosing regime. Additionally, the labeling on the blister packs may aid the patient in keeping track of whether medications have been taken.

Another example of an advance in prescription packaging is an individual medicament pouch or packet. Examples of individual medicament pouch/packets may be found in U.S. patent application Ser. No. 11/741,539 entitled "Serially Connected Packets with Grasping Portion" and in U.S. patent application Ser. No. 11/741,542 entitled "Serially Connected Packets with End Indicator." The total combination of medications that are prescribed may be filled into an individual medicament pouch or packet. A label may be affixed or printed directly onto the pouch that displays the time/day/date for ingestion and/or other dosing regime information, patient information, and medications contained inside the pouch. Thus, a patient need only port along the pouches that s/he will need during a specific time period. The patient need not determine what combination of pills needs to be taken at various times, as the individual filled pouches provide the groupings. The time/day/date label assists the patient in remembering whether or not the medicaments have been ingested or not.

Thus, a "multi-dose medicament container," as used herein, is a receptacle that holds a set of medications corresponding to one or more prescriptions of a patient, usually (but not necessarily) with overlapping dosing regimes, e.g., an intersection of dosing regimes so that multiple medication(s) may be packaged together. A multi-dose medicament container may have a single receptacle, such as a traditional prescription container or a pouch. A multi-dose medicament container may have multiple receptacles, such as a blister pack. Other types of multi-dose medicament containers may be possible. A "dosing regime," as used herein, is an indication of how to take pills in accordance with the directions on a prescription or medication directions. For example, a dosing regime may be "with an evening meal," "before or after a meal," "one capsule every other day on an empty stomach" and the like.

Filling the multi-dose blister packs, pouches, and other multi-dose medicament container configurations may be done manually or automatically. A "fill pattern," as used herein, is defined as a mapping of pills from one or more prescriptions of a patient into one or more receptacles of one or more multi-dose medicament containers. Fill patterns may be complex. For example, in the case of a blister pack, if Prescription A is required to be ingested once a day, and Prescription B is required to be ingested twice a day, the fill pattern may perform the appropriate mapping so that each labeled blister cell of the blister pack contains the appropriate combination of pills. A "morning" blister cell may be mapped to contain two pills, one of Prescription A and one of Prescription B. An "evening" blister cell may be mapped to contain only one of Prescription B's pills.

If Prescription C is added to a patient's medication regiment, but the duration of Prescription C is two weeks shorter than Prescriptions A and B, the mapping may become even more complex. Pills from prescription C may be mapped, for instance, to only the middle few rows of the blister packs corresponding to the dates of the duration of prescription C.

Problems with fill patterns, however, may occur when multiple differently sized and shaped pills are mapped to a single receptacle of a multi-dose medicament container. The necessary combination of pills to comply with one or more dosing regimes may not physically fit into a single blister cell, pouch or receptacle. Individual blister cells, pouches or receptacles of a multi-dose medicament container may require a sufficient air cushion so that pills are not crushed or punctured. A need exists for a method and system for determining a volume-based fill pattern of a multi-dose medicament container, so that the combined multiple pills fit appropriately into the container receptacles, the fill pattern is easily determined and communicated, and the benefits and ease of use of the multi-dose medicament containers for the patient are maintained.

BRIEF SUMMARY OF THE DISCLOSURE

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter.

As discussed in the Background, a "multi-dose medicament container" as used herein may be a receptacle that holds a set of medications or pills corresponding to one or more prescriptions of a patient, usually (but not necessarily) with overlapping dosing regimes, e.g., an intersection of dosing regimes so that one or more pills from the set may be packaged together. A "dosing regime," as previously discussed in the Background, may be an indication of how to take pills in accordance with the prescription directions. In addition to prescription medications, multi-dose medicament containers may also hold, for example, nutraceuticals, over-the-counter (OTC) medications, or some combination of thereof. The term "prescription," as used herein, is not only limited to a direction by a physician to a pharmacist for the preparation and use of a medicine or remedy. The term "prescription" as used herein may also refer to a nutraceutical that the patient is taking, an OTC medication that the patient is taking, or some combination of one or more of an OTC medication, nutraceutical and/or prescribed medication for the patient. Furthermore, in the present application, it is understood that one "prescription" may refer to one or more prescribed medications, nutraceuticals, and/or OTC medications.

Multi-dose medicament containers may be available in different types. For instance, a multi-dose blister pack may be one type of multi-dose medicament container used to fill one or more prescriptions for a patient. Examples of multi-dose blister packs may be found, for instance, in aforementioned U.S. Provisional Patent Application Ser. No. 60/947,169 entitled "Nested Multi-Dose Blister Pack." A medicament packet or pouch may be another type of multi-dose medicament container used to hold the set of pills to be packaged together per the pills' dosing regimes. Examples of individual packets/pouches may be found, for instance, in aforementioned U.S. patent application Ser. No. 11/741,539 and U.S. patent application Ser. No. 11/741,542. The disclosure of the present application may operate in accordance with these and other types of multi-dose medicament containers.

Methods and systems for filling multi-dose medicament containers are also known in the art. Aforementioned U.S. Provisional Patent Application Ser. No. 60/940,790 entitled "Multi-Dose Filling Machine and Process" discloses a system, or filling entity, for filling a multi-dose blister pack by using a press and one or more transfer fixtures. Said system uses intermediate cards containing single doses of prescribed medications to transfer pills into multi-dose blister packs. Other filling entities and methods for medicament pouches and other types of multi-dose medicament containers are also known in the art. A filling entity may be a mechanical system that is entirely automated by a computer network, it may be an entirely manual system with one or more human beings performing the filling of the prescriptions, or it may be some combination of automated and manual. The disclosure of the present application may also operate in accordance with these and other systems, entities, and methods for filling multi-dose medicament containers.

The instant application discloses a system and a method for determining and communicating a volume-based fill pattern for one or more multi-dose medicament containers. A "fill pattern," as introduced in the Background and used herein, is defined as a mapping of pills from one or more prescriptions of a patient to one or more multi-dose medicament containers based on some supplied parameter, where a single receptacle of the multi-dose medicament container(s) may be mapped to hold at least one pill from each of the one or more prescriptions whose dosing regimes overlap or whose pills may be packaged together. The fill pattern may result in a determination of the number of multi-dose medicament containers needed to completely fill the one or more prescriptions.

The system may include prescription information corresponding to one or more prescriptions of a patient to be filled using multi-dose medicament containers. The prescription information may indicate that one or more pills from each of the one or more prescriptions may be packaged together based on overlapping or intersecting dosing regimes. Prescription information for each different prescribed medication, nutraceutical, and/or OTC medication may include, but is not limited to, the name of the patient, the date of issue, the name of the prescribed medication, the dosage, the maximum number of pills per prescription, the duration of the prescription, the dosing regime, and other such standard prescription information.

The prescription information corresponding to the one or more prescriptions may be received by the system in any number of ways. Direct input of prescription information may be entered into the system by a physician, physician's assistant, nurse, pharmacist, pharmacy technician or other medical professional. Direct input of prescription information is not limited to a person entering the information, for instance, electronic entry, scanning or other automatic methods may be used to input prescription information. The prescription information may be requested from or automatically received over a computer network from a remote location. Alternatively, the prescription information may be downloaded or transferred from another site or data storage area. Any known method of inputting prescription information may operate in accordance with the present disclosure.

The system may also include a computer that receives the prescription information, determines the fill pattern, and communicates the determined fill pattern to a filling entity for filling of the prescriptions using multi-dose medicament containers. The computer may be physically located at a pharmacy store-front, mail-order location or otherwise in physical proximity to a filling entity. Or, the computer may be at another physical location or co-located with a web server so that communication with the filling entity is performed over a network. With advances in computer networking technology, many different network configurations and communication pathways to the filling entity are possible. Of course, "lower tech" methods of communicating a filling pattern are also possible, such as displaying the filling pattern on a screen for a person to read, print out, fax, or physically give to the filling entity.

The computer may be coupled to a storage device that contains pill data and multi-dose medicament container data. The storage device may be locally accessible or contained in the same machine as the computer. Alternatively, the storage device may be remote and accessed by the computer through a network. Or, a portion of the pill and/or container data may be stored locally, and another portion may be stored remotely. Again, with the advances in computer networking, many different configurations of data storage and data access by the computer are possible.

The pill data on the storage device may contain information for a variety of pills, including nutraceuticals, OTC medications and/or prescribed medications indicated by the one or more prescriptions of the patient. Pill data may include but is not limited to information such as pill identification information, strength of dosage, density, volume, chemical content, size, shape and physical dimensions of the pills. Pill data may also include auxiliary data such as dosing regime indications, labeling directions, patient preferences and/or notes, and the like. The container data may contain information corresponding to the types of containers available to be selected for use in prescription filling. Container data may include the type of container; the size, dimensions and/or volume of a receptacle of the container; the number of receptacles per container; and other data associated with each type of multi-dose medicament container.

To determine a volume-based fill pattern, the computer may receive prescription information listing the set of pills from the one or more prescriptions for a patient that are to be packaged together based on overlapping dosing regime(s). The prescription information may be received from a single source or from multiple sources. A selection may also be received at the computer that indicates if a volume-based fill pattern using cuboid volume is desired, or if a volume-based fill pattern using a packing parameter is desired.

The selection of a type of multi-dose medicament container may also be indicated, based upon type (e.g., pouch, pack, or other) and/or size of receptacle (e.g., pouch size, blister cell size, etc.). Selections may be received with the prescription information, they may be input by a technician per indication of the prescribing medical authority or the patient, or they may be pre-programmed into the system based on, for example, specific types of pills, durations of prescriptions, filling entities and/or other selection criteria. The type and/or size of multi-dose container may be optimized according to one or more factors. One such factor may include customer preference. For example, a pharmaceutical professional, patient, or patient's agent may indicate a preference for a type and/or size of medicament container(s), and/or a preference for what combination of pills s/he wishes to be filled into a specific receptacle of a container. Another factor of optimization may be based on a type of material of a medicament container. For instance, a certain pill's composition may indicate that the pill may be optimally stored in a plastic container, whereas a different pill's composition may indicate that the different pill may be optimally stored in a foil pouch. Yet another example of optimization may include determining a type and/or size of medicament container based on size of pills. Consider an example where five pills are desired to be packaged together, and the five pills may fit into two "large" sized multi-dose blister packs, four "medium" sized multi-dose blister packs, two "small" and one "large" multi-dose sized blister packs, or (in an example of mixing types of containers) a "large" sized multi-dose blister pack and a pouch. The packaging of the five pills may be selected by determining which alternative results in a minimum air space or cushion. Other factors may also be used alternatively or additionally to optimize the selection of a type and/or size of multi-dose medicament container(s).

The computer may then access the storage device to obtain the pill data for each of the prescribed pills and the container data for the desired type of multi-dose container.

If a volume-based fill pattern using cuboid volume is indicated, the computer may use the obtained pill data to determine the cuboid volume for each of the pills that are to be packaged together. The "cuboid volume" of a single pill, as used herein, is a representation of the volume of the pill in a cuboid, i.e., a selected three-dimensional shape that the pill would fit into based on the physical dimensions of the pill. The shape may be, for example, a rectangular solid, a spherical solid, a cubical solid, or a solid of any other three-dimensional shape. The shape may be selected based on minimizing air space in a container or packaging element that holds the pill. The selected three-dimensional shape may be, for example, a smallest three-dimensional shape into which the pill may fit. The total cuboid volume of the set of pills to be packaged together may be determined by summing the individual cuboids for the set of pills. The dimensions of the indicated multi-dose medicament container may be obtained from the container data, and the maximum number of cuboids for the set of pills that may fit into the multi-dose medicament container may be determined, thus determining the "cuboid volume" of the multi-dose medicament container corresponding to the pill. The determined fill pattern may then be communicated to the filling entity.

Consider the example of using a multi-dose blister pack as the container selection for a volume-based fill pattern using cuboid volume. Each blister cell on the multi-dose blister pack may be similarly-sized, with the dimensions of the cell and the number of cells per pack stored in the storage device and obtained from the storage device by the computer. Alternatively, each blister cell may be differently sized to optimize for other demands, such as a specific combination of prescribed medications, nutraceuticals and/or OTC medication for a patient; patient request of card configuration (e.g., weekly packs, daily packs, or other); or other criteria. The computer may obtain the pill data for each of the medications indicated by the prescription information that are to be packaged together based on dosing regimes. The computer may then determine the cuboid volume of each of the pills, and sum the cuboids to obtain a total cuboid pill volume. The total cuboid pill volume may then be divided by the cuboid volume of an individual blister cell to determine the total number of blisters by volume. The total number multi-dose blister packs by volume (TNPV) that are needed to fill the one or more prescriptions whose pills are to be packaged together may be determined based on the total number of blisters by volume and an indicated number of multi-dose filled blisters per pack. The indicated number of multi-dose filled blisters per pack may be obtained, for example, from memory or from a user input.

Each blister cell if separable, however, may have a backing of finite size on which to print labeling information. As the individual blister cells may be perforated and separated from the pack, the backing of each individual blister cell is required by the laws of most jurisdictions in the United States of America to be labeled with particular information regarding its contents. The maximum number of pills per blister may be limited by the space needed to print the required labeling information on the backing of the individual blister cell. Therefore, the computer may also determine a total number of multi-dose blister packs by print space (TNPP) needed to fill the one or more prescriptions. The TNPP may be determined based on the total count of different pill identifications to be packaged together based on dosing regime, the maximum number of pill identifications able to be printed onto the blister backing as limited by the available printing space on the blister, and an indicated number of multi-dose blisters to be filled per pack.

Having determined the TNPV and the TNPP, the computer may then determine the volume-based fill pattern using cuboid volume by taking the greater of TNPV and TNPP, and may thus arrive at a number of multi-dose blister packs needed to fill the one or more prescriptions. The determined fill pattern may then be communicated to the filling entity by any of the alternatives as previously described above.

If a volume-based fill pattern using a packing parameter is indicated, the computer may obtain the pill volume for each of the set of pills from the one or more prescriptions required or desired to be packaged together based upon dosing regimes. The term "pill volume," as used herein, may include the volume of a pill in any volumetric form, including but not limited to exact pill volume, estimated pill volume, actual pill volume, measured pill volume, determined pill volume (e.g., by calculation, scanning, visual identification, or other means), obtained pill volume (e.g., from a database or received via data entry), cuboid pill volume, and/or any other form of representing the volume of a pill. Container data may also be obtained from the storage device by the computer. The computer may then determine a target fill volume of the multi-dose medicament container by using the volume of a receptacle of the container modified by the packing parameter. A "packing parameter," as used herein, is a parameter that places a restriction on how a receptacle of a medicament container is filled or packed. A "target fill volume," as used herein, is a desired maximum volume of fill of the receptacle of the container. For example, if the packing parameter is a percentage fill by volume, then the target fill volume is determined by restricting the maximum fill volume of the container receptacle to the percentage fill indicated by the packing parameter. Other types of packing parameters may also be used to modify the target fill volume.

The packing parameter may be stored in the computer or in the storage device a priori, or it may be input or modified by an operator. There may be a different packing parameter for each different type of multi-dose medicament container, or different packing parameters used for different types and/or combinations of pills. For instance, a specific multi-dose medicament container made out of a specific type of material may require more or less total fill based on material properties. Or, a gel-type pill may require more air cushion to minimize chances of rupture.

The total pill volume of the set of pills to be packaged together based on dosing regimes may be determined, and then may be compared to the determined target fill volume of the indicated medicament container receptacle. If the total pill volume of the set of pills is greater than the target fill volume of the container receptacle, then the computer may determine how many multi-dose container receptacles are needed to fill the one or more prescriptions, i.e., the volume-based fill pattern, and communicate the fill pattern to the filling entity.

Again consider the example of a multi-dose blister pack, but this time for a volume-based fill pattern using a packing parameter. The computer may obtain, from the storage device, an individual pill volume for each of the pills indicated by the prescription information that have at least one portion of intersecting dosing regimes. The computer may then determine the total pill volume for the set of pills by summing the individual pill volumes. Next, the computer may determine the target fill volume of an individual blister cell by restricting the individual blister cell volume by the packing parameter. The total pill volume may then be divided by the target fill volume of an individual blister cell to determine a total number of blisters by volume. The total number of multi-dose blister packs by volume (TNPV) that are needed to fill the one or more prescriptions may be determined based on the total number of blisters by volume and an indicated number of multi-dose filled blisters per pack. The indicated number of multi-dose filled blisters per pack may be obtained, for example, from memory or from a user input.

As discussed earlier, for multi-dose blister packs, the maximum number of pills per blister may be capped by the space needed to print the required information onto the backing of an individual blister cell. The computer may determine the total number of multi-dose blister packs by printing space (TNPP) that are needed to fill the set of pills to be packaged together based on dosing regime(s) for the complete duration of the one or more prescriptions. The TNPP may be determined based on the total number of different pill identifications for the set of pills to be packaged together, the maximum number of pill identifications able to be printed onto the blister pack backing (as limited by available printing space), and an indicated number of multi-dose blisters to be filled per pack.

The computer may determine the volume-based fill pattern using a packing parameter by taking the greater of TNPV and TNPP, and thus may arrive at a number of multi-dose blister packs needed to fill the one or more prescriptions for the given dosing regimes. This determined fill pattern may then be communicated to the filling entity by any of the alternatives as previously described above.

DETAILED DESCRIPTION OF THE PREFERRED EMBODIMENTS

Although the following text sets forth a detailed description of numerous different embodiments, it should be understood that the legal scope of the description is defined by the words of the claims set forth at the end of this patent and equivalents. The detailed description is to be construed as exemplary only and does not describe every possible embodiment since describing every possible embodiment would be impractical. Numerous alternative embodiments could be implemented, using either current technology or technology developed after the filing date of this patent, which would still fall within the scope of the claims.

It should also be understood that, unless a term is expressly defined in this patent using the sentence "As used herein, the term '_____' is hereby defined to mean . . . " or a similar sentence, there is no intent to limit the meaning of that term, either expressly or by implication, beyond its plain or ordinary meaning, and such term should not be interpreted to be limited in scope based on any statement made in any section of this patent (other than the language of the claims). To the extent that any term recited in the claims at the end of this patent is referred to in this patent in a manner consistent with a single meaning, that is done for sake of clarity only so as to not confuse the reader, and it is not intended that such claim term be limited, by implication or otherwise, to that single meaning. Finally, unless a claim element is defined by reciting the word "means" and a function without the recital of any structure, it is not intended that the scope of any claim element be interpreted based on the application of 35 U.S.C. §112, sixth paragraph.

Figure 1:
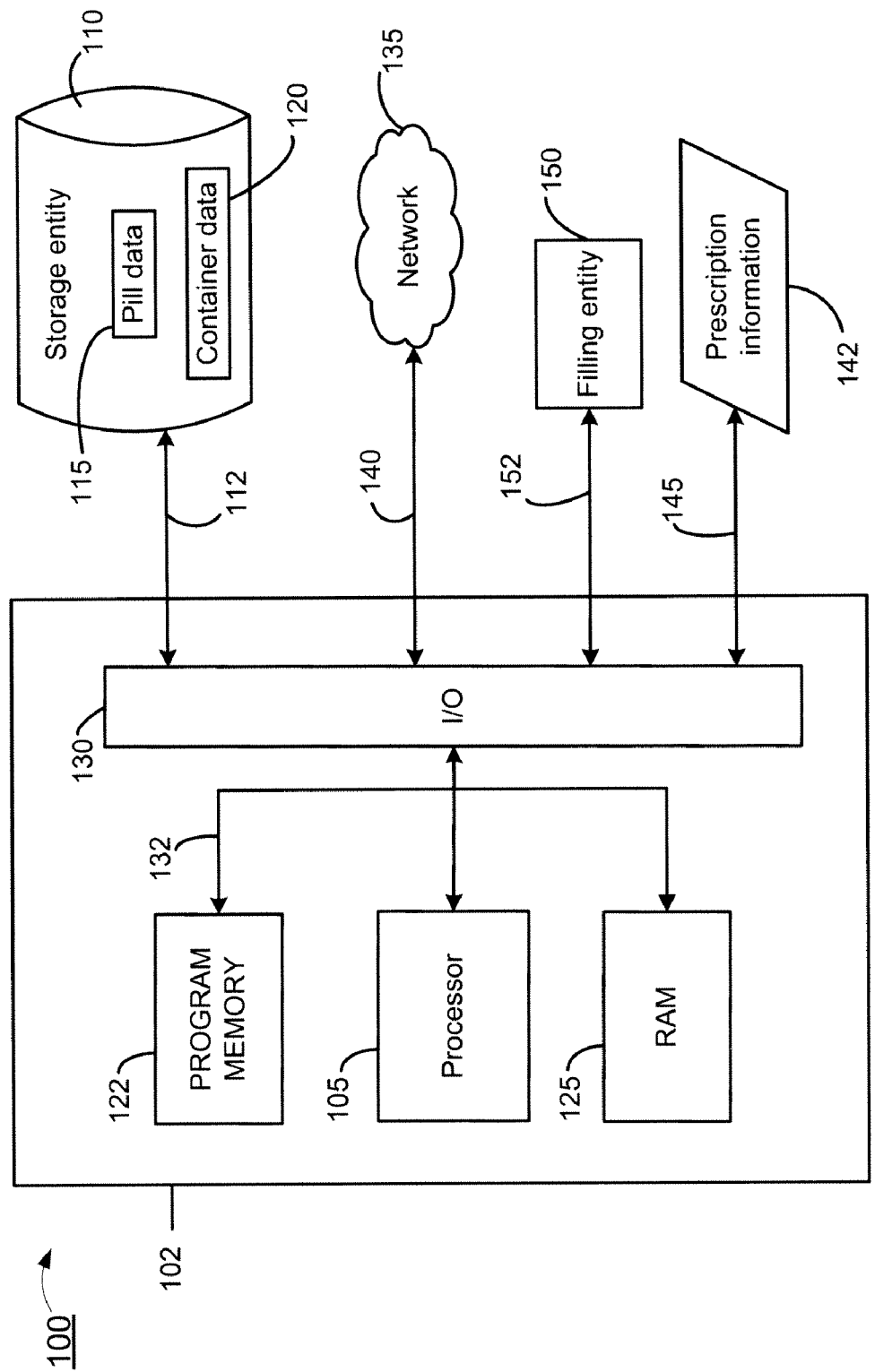
FIG. 1 is an embodiment of a system for determining and communicating a volume-based fill pattern of a multi-dose medicament container.

FIG. 1 is an embodiment of a system 100 for determining and communicating a volume-based fill pattern of a multi-dose medicament container. For the sake of illustration, a simplified block diagram of a computer 102 is used to illustrate the principles of the instant disclosure. However, such principles apply equally to other electronic devices, including, but not limited to, cellular telephones, personal digital assistants, media players, appliances, gaming systems, entertainment systems, set top boxes, and automotive dashboard electronics, to name a few. The computer 102 may have a processor 105 that is operatively connected to a database or storage entity 110 via a link 112. Link 112 may be as simple as a memory access function, or it may be a wired, wireless, or multi-stage connection through a network. Many types of links are know in the art of networking and are possible. Alternatively, the storage entity 110 may be contained in the same entity as the computer 102. It should be noted that, while not shown, additional databases may be linked to the computer 102 in a known manner. The storage entity 110 may include any data that may be relevant to determining a fill pattern for a multi-dose medicament container, such as but not limited to pill data 115 and container data 120.

Pill data 115 may contain facts about pills that are available to be prescribed. The pill data 115 may include pill identification information, such as an identification indication, trade name, generic name, chemical composition, dosage units, and the like. The pill data 115 may also contain physical attributes, such as shape, color, length, width, height, diameter, volume, density, weight, form (such as tablet, gel, chewable) and the like. Pill data may also include auxiliary data such as dosing regime indications, labeling directions, patient preferences and/or notes, and the like. Container data 120 may contain facts about the containers, such as but not limited to: type, dimensions, volume, material from which it is made, whether or not there are multiple receptacles in the container and if so, how many and what size, etc. Pill data 115 and/or container data 120 may be obtained by the computer 102 through a download, data transfer, or other such mechanism. Pill data 115 and/or container data 120 may be obtained by the computer 102 through an identification system that may automatically determine the identity and characteristics of a pill and/or a container. Alternatively, the computer 102 may request or read the storage device 110 to obtain only the specific pill data 115 and container data 120 that it needs to fill a specific set of prescriptions. Any known method of obtaining pill data 115 and container 120 may be used in accordance with the present application.

The computer 102 may include a processor 105 (may be called a microcontroller or a microprocessor) for executing computer executable instructions, a program memory 122 for permanently storing data related to the computer executable instructions, a random-access memory (RAM) 125 for temporarily storing data related to the computer executable instructions, and an input/output (I/O) circuit 130, all of which may be interconnected via an address/data bus 132. It should be appreciated that although only one processor 105 is shown, the computer 102 may include multiple processors 105. Similarly, the memory of the computer 102 may include multiple RAMs 125 and multiple program memories 122. Although the I/O circuit 130 is shown as a single block, it should be appreciated that the I/O circuit 130 may include a number of different types of I/O circuits. The RAM(s) 125 and program memories 122 may be implemented as semiconductor memories, magnetically readable memories, and/or optically readable memories, for example. The computer 102 may also be operatively connected to a network 135 via a link 140. Similar to link 112, the form of link 140 may take any form known in the art of networking.

The computer 102 may receive prescription information 142 over a link 145. Link 145 may be the same entity as network link 140 or database link 112, or it may be a separate entity. Link 145 may be an operator/user interface, or it may be a local or remote network connection to a server, website, other computer, or a different database. The computer 102 may receive prescription information 142 from a plurality of sources, for example, when a single computer 102 receives prescription information 142 from multiple medical entities such as doctors' offices, hospitals, and the like. In this case, multiple links 145 are possible.

The computer 102 may also be operatively connected to a filling entity 150 via a link 152 for communicating fill patterns. Filling entity 150 may dispense medications according to the fill pattern received from computer 102 so that the prescription(s) are filled into one or more multi-dose medicament containers. Filling entities 150 may be automatic processes or systems, they may be manual, or some combination of the two. Multiple links 152 to multiple filling entities 150 may be possible, for instance, if separate filling entities exist for different types of medicament containers, or if a single computer 102 determines fill patterns for multiple pharmacy storefronts, each with its own filling entity 150. Link 152 may be the same link as links 112, 140 or 145, or it may be a separate link. Link 152 may also be a local connection or a remote connection through network 135.

Figure 2:
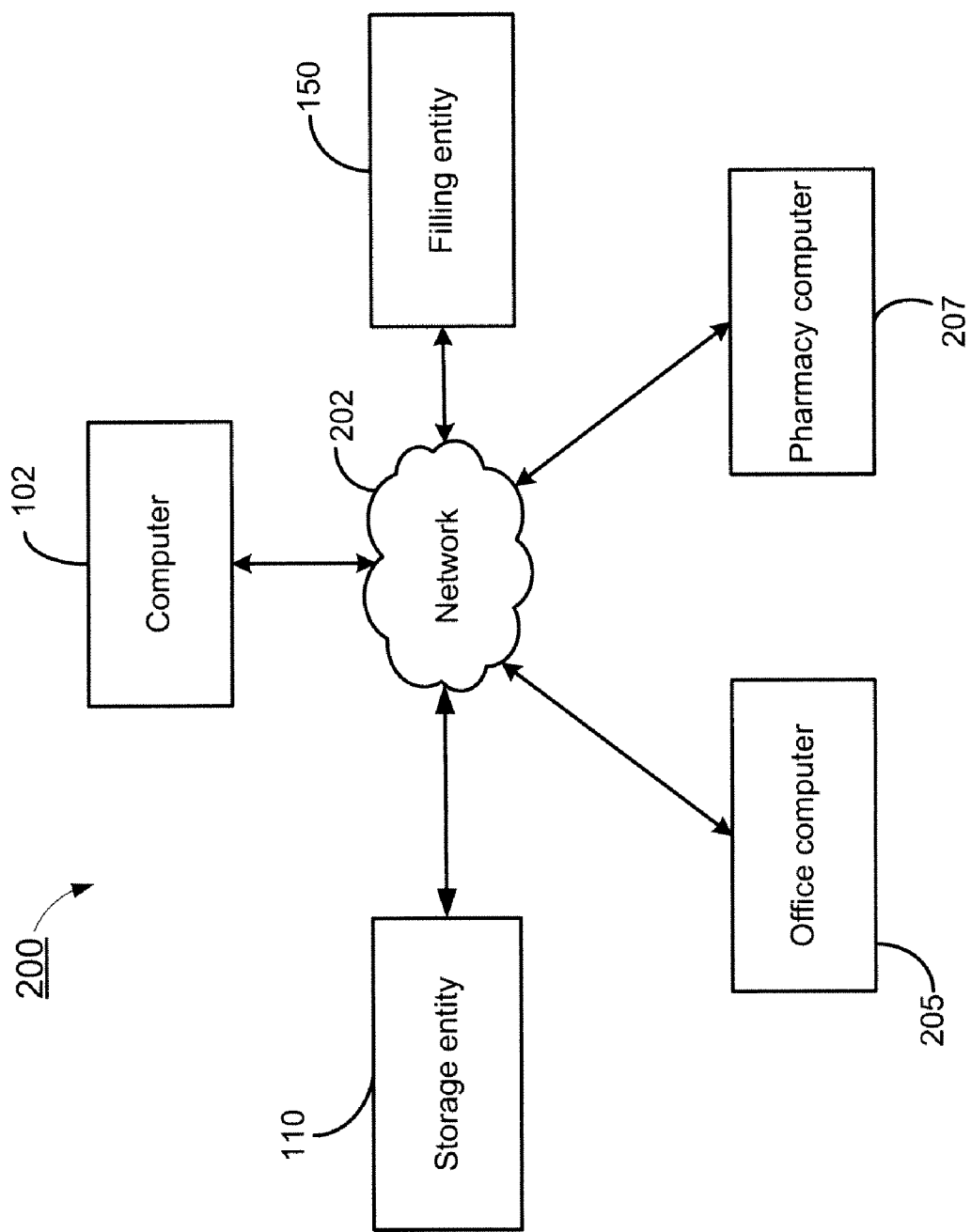
FIG. 2 is an alternate embodiment of the system distributed in a network.

FIG. 2 illustrates an alternate embodiment of the system 200 distributed in a data network 202. The network 202 may be provided using a wide variety of techniques well known to those skilled in the art for the transfer of electronic data. For example, the network 202 may comprise dedicated access lines, plain ordinary telephone lines, satellite links, combinations of these and any other component to facilitate the communication of information between a plurality of network nodes. Additionally, the network 202 may include a plurality of network computers or server computers (not shown), each of which may be operatively interconnected in a known manner. Where the network 202 comprises the Internet, data communication may take place over the network 202 via an Internet communication protocol. Data sent over network 202 may be encrypted for security and privacy purposes.

The computer 102 may take the form of a server computer, as commonly known in the networking art. For instance, if computer 102 is a website server, a medical professional may access the website hosted by computer 102 from their own local office computer 205 in order to enter a patient's prescription information for filling.

The computer 102 may communicate via network 202 to other entities. The computer 102 may receive prescription information via network 202 from an office computer 205 or pharmacy computers 207. Office computers may be located in doctors' offices, hospitals, or other medical facilities. Pharmacy computers may be located in a pharmacy storefront, hospitals, a distribution center such as for a mail-order pharmacy or other facilities that dispense medication. The computer 102 may access a database or storage entity 110 via network 202 to obtain pill data and container information, and communicate desired fill patterns to filling entity 150 via network 202.

Although only one computer 102, office computer 205, pharmacy computer 207, storage entity 110 and filling entity 150 are illustrated in FIG. 2, it should be understood that different numbers of computers 102 205 207, databases 10 and filling entities 150 may be utilized. For example, the network 202 may include a plurality of computers 102 and hundreds of offices 205 and pharmacies 207, all of which may be interconnected via the network 202. Multiple databases 110 may be employed for data storage. Multiple filling entities 150 may be served. According to the disclosed example, this configuration may provide several advantages, such as, for example, enabling load distribution of determining fill patterns across several computers 102, or enabling near real time uploads and downloads of information as well as periodic uploads and downloads of information for batch processing. This may provide for a primary backup of all the information generated in the process of updating and accumulating filling pattern data.

Figure 3:
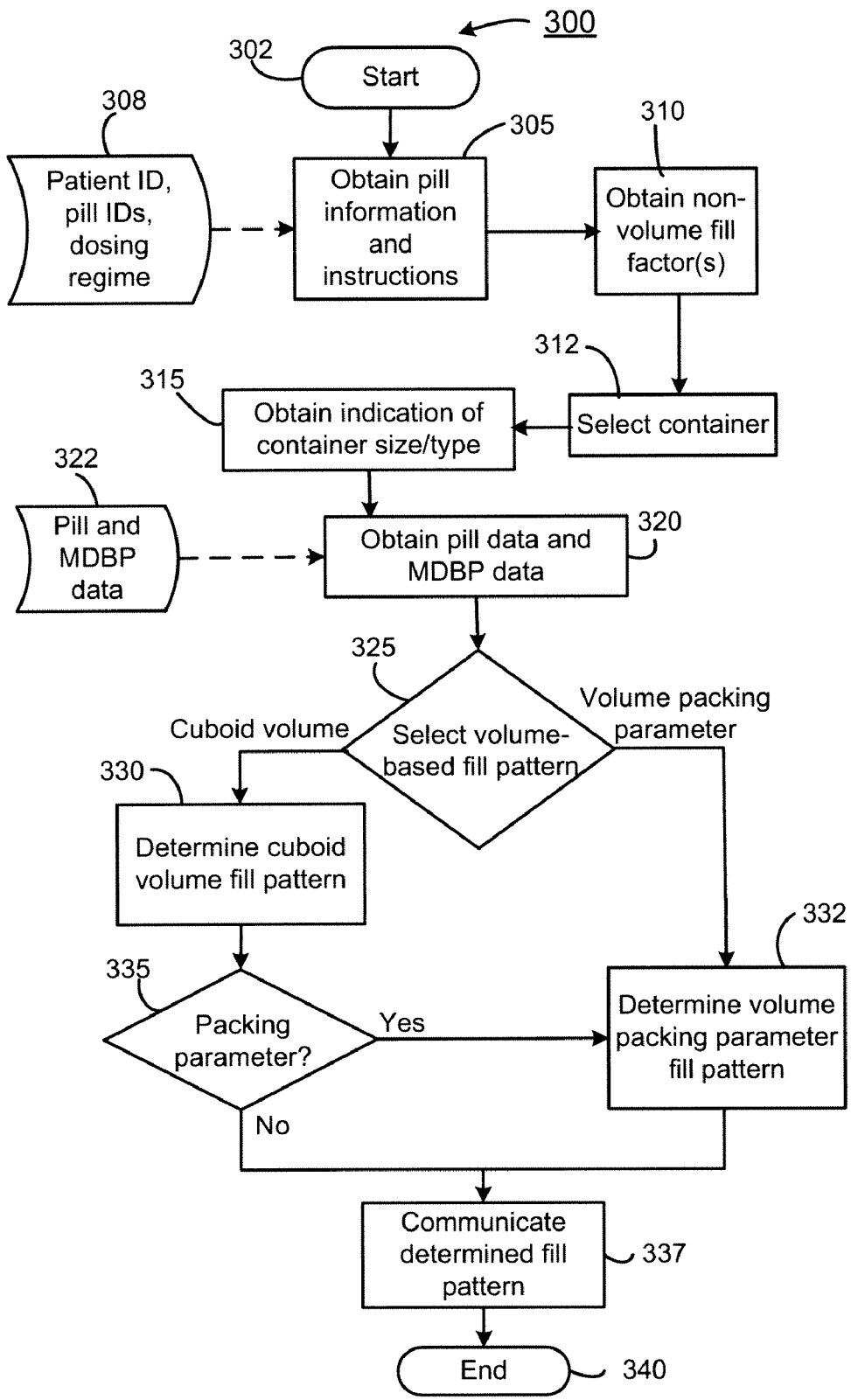
FIG. 3 illustrates an exemplary method of determining and communicating a volume-based fill pattern for a multi-dose medicament container.

FIG. 3 illustrates an exemplary method 300 of determining and communicating a volume-based fill pattern for a multi-dose medicament container. In this embodiment, the multi-dose medicament container is a multi-dose blister pack (MDBP), although the method 300 is equally applicable to other types of multi-dose medicament containers. At the start 302, pill instructions may be obtained 305. The pill instructions may be for one or more prescribed medications for a patient, one or more nutraceuticals for the patient, and/or one or more OTC medications for the patient, or some combination of the three. The pill instructions 305 may include a patient identification, an identification of the pill and a dosing regime (block 308). Pill instructions 305 for a pill that is a prescribed medication may be obtained, for example, from a prescription (block 308) for the prescribed medication. Pill instructions 305 for a nutraceutical or an OTC medication may be obtained, for example, from labeling of the nutraceutical or OTC medication (block 308) and may not include a patient identification.

Next, one or more non-volume fill factors may be obtained (block 310). A non-volume fill factor may include, for example, an indication of a drug interaction between two pills that may influence whether or not the two pills should be packaged into a same receptacle. The drug interaction may be a chemical interaction, such as a potential undesirable chemical interaction that may occur if two pills are in physical proximity. The drug interaction may be a physical interaction, for instance, if one pill is formed in a way that may damage another pill. Other types of drug interactions may be possible.

Another non-volume fill factor may include, for example, an indication of a user selection. For instance, a user may desire to minimize the number of MDBPs and have "overflow" medications from a fill pattern packaged into a pouch instead of an entire other MDBP. A user may desire to have multi-dose medicament containers filled for each week, have multi-dose medicament containers filled for different times of day, or have multi-dose medicament containers configured by some other criteria. Or, a user may desire to have pills of a certain characteristic packaged into a same receptacle of a multi-dose medicament container, for instance, pills of specific colors, pills that need to be taken with food, pills that are chewable, etc. Other non-volume fill factors may be possible and obtained at block 310.

Non-volume fill factors may be obtained (block 310) via any known means such as data entry, data query, download, calculation from other data, and other means. Non-volume fill factors may obtained (block 310) in accordance with embodiments of system 100 of FIG. 1 and/or embodiments of system 200 of FIG. 2.

After obtaining one or more non-volume fill factors (block 310), a multi-dose medicament container may be selected (block 312) based upon the obtained non-volume fill factors. The selection may include type(s) of multi-dose medicament container(s), size(s) of multi-dose medicament container(s), size(s) of a receptacle of a multi-dose container(s), and/or other criteria.

An indication of the selected multi-dose blister pack to be used may be received at block 315 from block 312. In some embodiments, obtaining non-volume fill factor(s) (block 310) and selecting a container based on the fill factors (block 312) may be omitted. For those embodiments, an indication of a container size and/or type may be obtained (block 315) directly after obtaining pill information and instructions at block 305.

In this embodiment, an indication of an MDBP with uniformly sized blister cells of a specific size may be obtained. In another embodiment, an indication of an MDBP with varying sizes of blister cells may be obtained. For example, for a weekly MDBP supporting a dosing regime of four times of day, a selection may be obtained for a large cell for the morning and a small cell for noon, evening and night. In a more general embodiment, an indication of a selection from among different types and/or sizes of multi-dose medicament containers, such as multi-dose blister packs, pouches, or other types of containers may be obtained. (Note that if method 300 is applied to a system with only one available type and size of multi-dose medicament containers, then block 315 may be optional.) The selection may be received via the I/O interface 130 of FIG. 1, the selection may be received with the prescription information 308, or the selection may be loaded a priori based upon a selection criteria such as type of pill, type of filling entity, duration of prescription, and the like.

Pill data corresponding to the pills identified in the prescription information and the container data of the indicated multi-dose medicament container may be obtained 320 from a storage device containing the data 322. As previously discussed, pill data 322 may include but is not limited to information such as pill identification information, strength of dosage, density, volume, chemical content, size, shape and physical dimensions of the pills. Pill data 322 may also include auxiliary data such as dosing regime indication, labeling directions, patient preferences, notes, and the like. Container data 322 may include information corresponding to the type of container; the size, dimensions and/or volume of one or more receptacles of the container; the number of receptacles and their configuration for the container; and other data. At least some portion of the pill data 322 and at least some portion of the container data 322 may be obtained via any known means such as data entry, data query, download, calculation from other data, real-time or a priori scanning, a pill identification system, a container identification system, and other means.

At block 325, a selection of volume-based fill pattern may be made using any of the selection methods described above. Based on the selection, the volume-based fill pattern is determined by using a cuboid volume 330 or by using a packing parameter 332. Both blocks 330 and 332 are more fully described in subsequent sections. If, at block 325, a volume-based fill pattern based on packing parameter is selected, a volume packing parameter fill pattern may be determined 332. If, at block 325, a cuboid volume fill pattern 330 is selected, the cuboid volume fill pattern may be determined 330. If the cuboid volume fill pattern additionally requires a packing parameter as determined at block 335, the method may proceed to block 332. Note that method 300 may be implemented for only one option of volume-based fill pattern, either by using cuboid volume 330 or by using a packing parameter 332. In that case, the decision at block 325 may be omitted and the method may proceed directly to block 330 or block 332. In another embodiment, block 335 may be omitted if a packing parameter is not used with a cuboid volume. In yet another embodiment, blocks 325, 330, 332 and 335 may be omitted, for instance, when the fill pattern is determined by non-volume fill factors. Finally, the determined fill pattern may be communicated to the filling entity 337 and the method may end 340.

Figure 4:
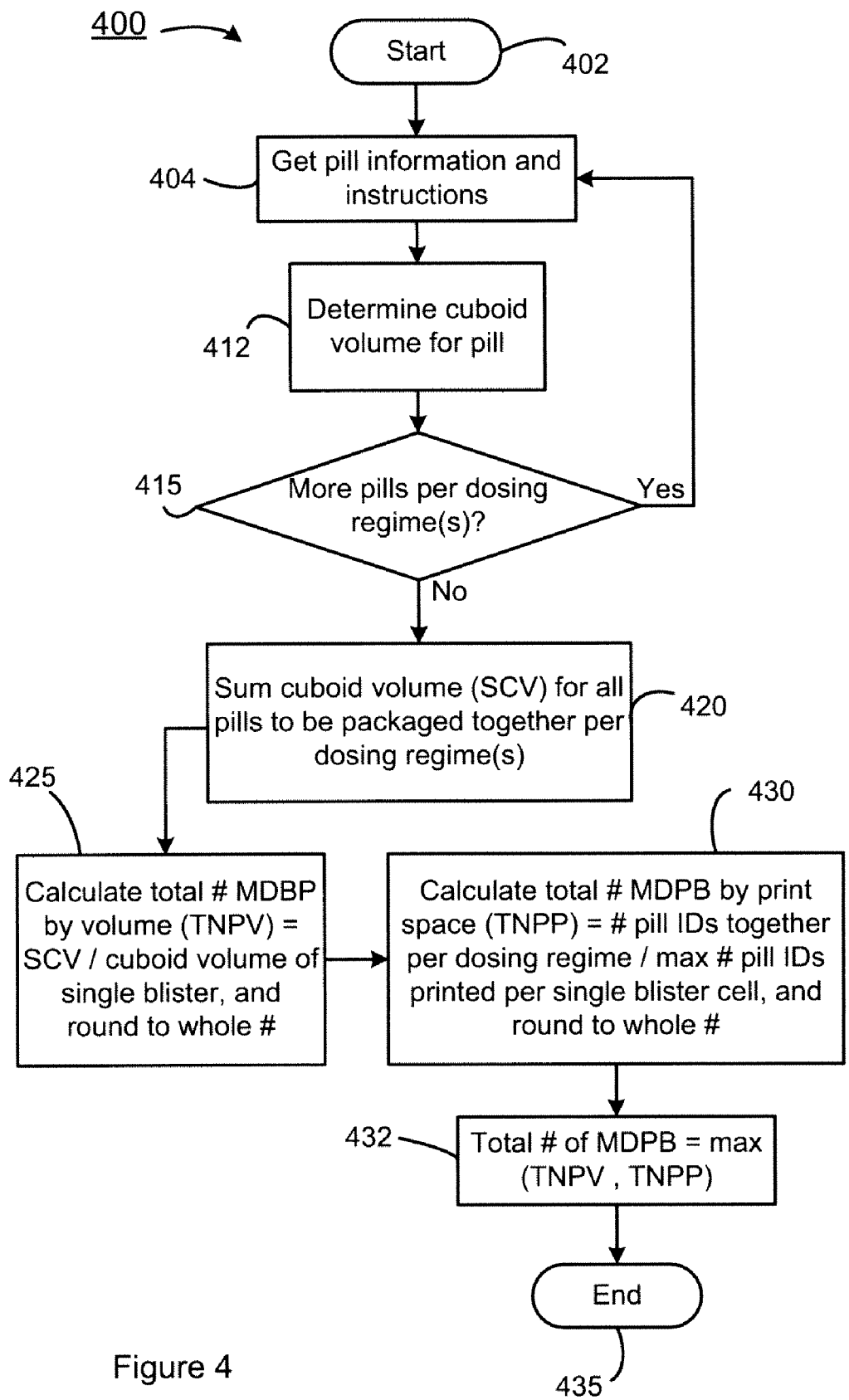
FIG. 4 shows an exemplary embodiment of a method for determining a volume-based fill pattern using cuboid volume.

FIG. 4 shows an exemplary embodiment of a method 400 for determining a volume-based fill pattern using cuboid volume such as in block 330 of FIG. 3. For this embodiment, again consider a multi-dose blister pack (MDBP). At the start 402, a pill identification may be obtained for the set of pills from a prescription identified to be packaged together (block 404). As previously discussed, a "prescription" as used herein may refer to a direction by a physician to a pharmacist for the preparation and use of a medicine or remedy. The term "prescription" as used herein may also refer to the use of a nutraceutical, an OTC medication, or some combination of one or more of a prescribed medication, nutraceutical and/or OTC medication for the patient. Pill instructions for the pill including pill identification and dosing regime may be obtained from an actual prescription issued by a medical professional, or in the case of a nutraceutical or OTC medication, may be obtained from labeling for the pill.

The pill's cuboid volume may then be determined at block 412. As previously discussed, the cuboid volume of a single pill is a representation of the volume of the pill in a cuboid, i.e., a selected three-dimensional shape into which the pill would fit based on the physical dimensions of the pill. The cuboid volume may be determined 412 in any number of ways, including but not limited to data entry, direct data retrieval such as from block 322 of FIG. 3, calculation based on pill data such as data from block 322 of FIG. 3, calculation based on other data, real-time determination based on an identification system, approximation, and/or other ways of determination.

If there are additional pills as indicated by the one or more prescriptions that are required or desired to be packaged together based upon their dosing regimes as determined in block 415, their identifications may be obtained 404 and their cuboid volumes may also be determined 412. After all of the pills' individual cuboid volumes are determined, the individual cuboid volumes may be summed at block 420 to obtain a sum cuboid volume (SCV) for the complete set of pills to be packaged together.

At block 425, a total number of packs by volume (TNPV) may be determined based on a total number of blisters by volume and an indicated number of multi-dose filled blisters per MDBP. The total number of blisters by volume may be determined by dividing the SCV by the cuboid volume of a single blister of the multi-dose blister pack, and rounding to a whole number. The cuboid volume (or, alternatively, the dimensions needed to calculate the cuboid volume), may have been determined, for example, in block 320 of FIG. 3 or determined using data from block 322 of FIG. 3.

As discussed in the Summary, the maximum number of pills per blister cell may be limited by the available space for labeling information on the backing of an individual blister cell. At block 430, a total number of blisters by print space may be determined by dividing the total number of different pill identifications for the set of pills to be packaged together by the maximum number of pill identifications able to be printed on available labeling space, and rounding to a whole number. The maximum number of pill identifications able to be printed, as limited by available printing space, may be obtained, for instance, from container data such as block 322. The TNPP (total number of packs by print space) may be determined based on the total number of blisters by print space and an indicated number of blisters to be filled per MDBP.

The fill pattern of the multi-dose blister packs for the one or more prescriptions may then be determined 432 by taking the greater of TNPV and TNPP. The method 400 may end 435.

Figure 5:
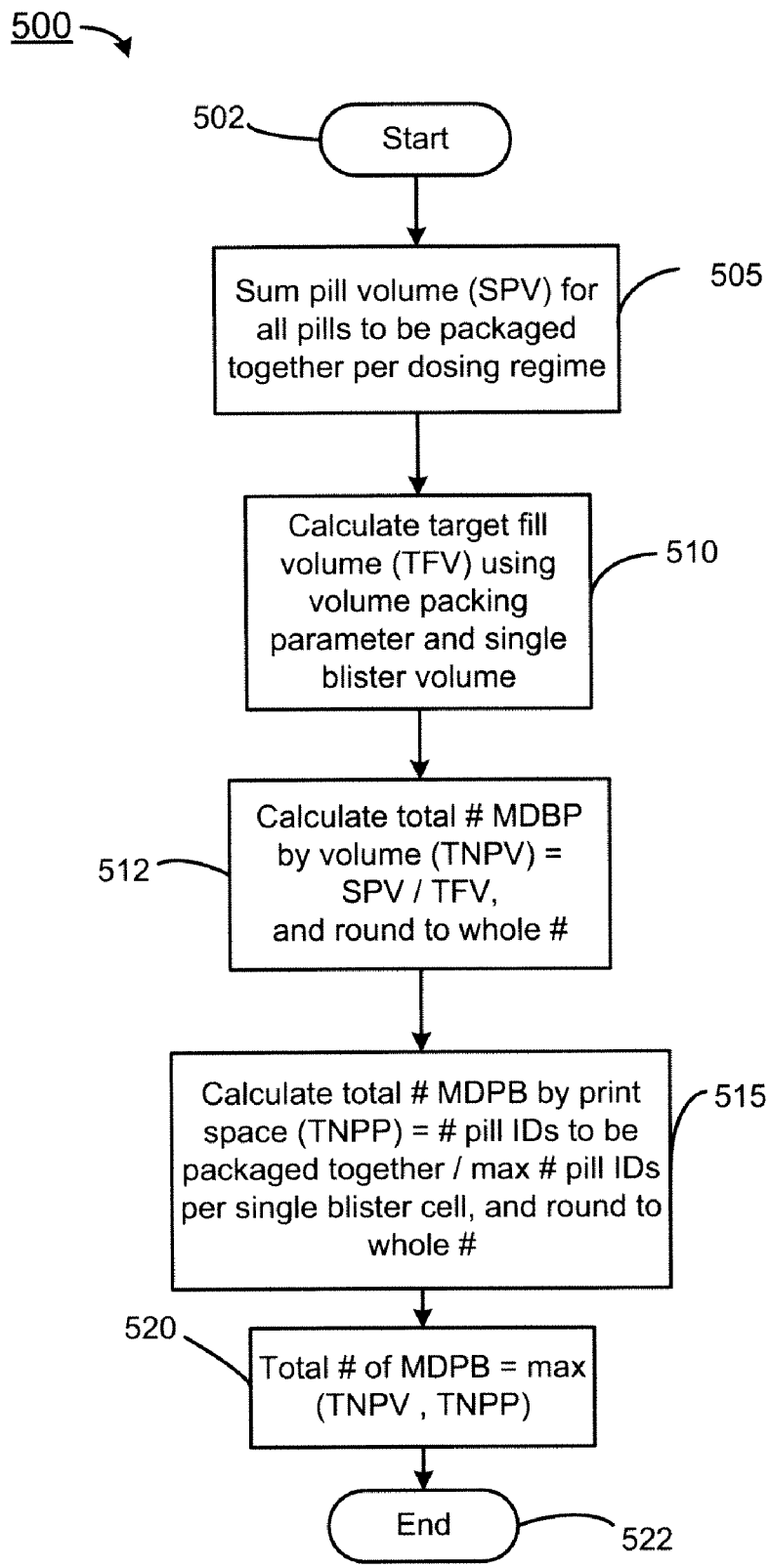
FIG. 5 illustrates an exemplary embodiment of a method for determining a volume-based fill pattern using a packing parameter.

FIG. 5 illustrates an exemplary embodiment of a method 500 for determining a volume-based fill pattern using a packing parameter. At the start 502, a total pill volume may be obtained by summing the individual pill volumes (SPV) for all of the medications/pills from one or more prescriptions of a patient that are required or desired to be packaged together based upon at least a portion of intersection of their respective dosing regimes 505. As previously discussed, an individual pill volume may include the volume of a single pill in any volumetric form, including but not limited to exact pill volume, estimated pill volume, actual pill volume, measured pill volume, determined pill volume (e.g., by calculation, scanning, visual identification, or other means), obtained pill volume (e.g., from a database or received via data entry), cuboid pill volume, and/or any other form of representing the volume of a pill. The individual pill volumes may have been obtained, for example, from reading a database as described in block 322 of FIG. 3, may have been calculated by a pill identification system, may have been entered via data entry, or obtained from other means. Next, a target fill volume (TFV) may be calculated 510 by using the volume packing parameter and a single blister volume. As discussed in the Summary, a volume packing parameter may place a restriction on the fill volume of a single receptacle, e.g., a percentage fill. The volume packing parameter may be input into the system, it may exist in the system a priori, or a loaded packing parameter may be modified by the operator. A packing parameter may vary based upon the type of container, the pill or type of pill, the size of a receptacle, a combination of factors, or other factors. The single blister volume, or dimensions leading to the calculation thereof, may have been obtained, for example in block 320 of FIG. 3.

At block 512, a total number of multi-dose blister packs by volume (TNPV) may be calculated by first dividing the sum of the pill volumes (SPV) by the target fill volume (TFV) for a single blister cell and rounding to a whole number to obtain a total number of blisters by volume, and then calculating TNPV based upon the total number of blisters by volume and an indicated number of multi-dose filled blisters per pack. As printing space is limited on the backing of an individual blister cell, a total number of multi-dose blister packs by print space (TNPP) may be calculated in block 515 by dividing a total number of blisters by print space by an indicated number of blisters to be filled per MDBP. The total number of blisters by print space may be determined based on the total number of different pill identifications for the set of pills to be packaged together and the maximum number of pill identifications able to be printed onto the labeling space. The maximum number of pill identifications able to printed on a given label or backing, as limited by available printing space, may be obtained from the container data.

Finally, the total number of multi-dose blister packs needed to fill the one or more prescriptions may be determined by taking the greater of TNPV and TNPP 520, and the method 500 may end 522.

It should be noted that although methods 300, 400 and 500 as illustrated by FIGS. 3, 4 and 5, respectively are discussed with respect to a multi-dose blister pack medicament container with same-sized blisters, the methods are not limited to the disclosed embodiments. The methods apply equally to other types of multi-dose medicament packages as well. A multi-dose blister pack medicament container with varying-sized blisters may be used. In this embodiment, the method may be used for each blister on the pack, and the filling pattern may be optimized across the set of blisters on the pack. In another embodiment, the methods may operate in accordance with the selection of number and/or sizes of multi-dose medicament containers may be made based upon sizes of pills to be packaged together, e.g., for a given set of pills to be packaged together, a selection of the number and/or sizes of medicament containers may be made based upon minimization of resultant air space or cushion in each blister. In another embodiment, if the multi-dose medicament container selected is a multi-dose medicament pouch, the calculations concerning a single pouch may be substituted for the calculations for a single blister cell.

In one embodiment, a patient may indicate a preference for the filling pattern and/or for a desired size and/or type of multi-dose medicament container. In another embodiment, a selection of multi-dose medicament container may be made based on a type of material of the container. For instance, a certain pill's composition may indicate that the pill may be optimally stored in a plastic container, whereas a different pill's composition may indicate that the different pill may be optimally stored a foil pouch. The methods of the present disclosure may operate in accordance with these embodiments. Other embodiments are possible. Each embodiment may be used individually or in conjunction with another embodiment. One skilled in the art may easily adapt methods 300, 400 and 500 to various types of multi-dose medicament containers and different embodiments.

Figure 6:
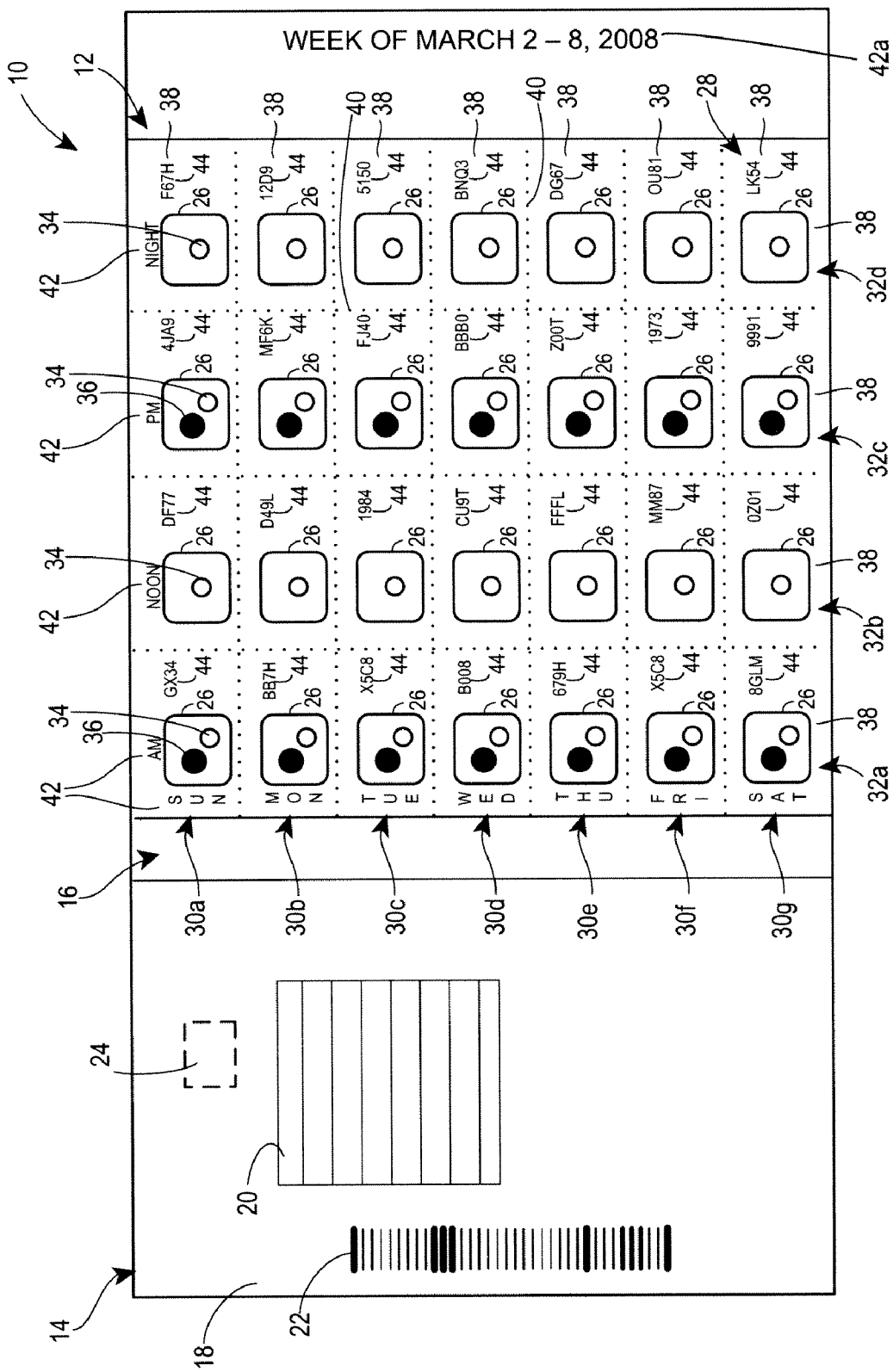
FIG. 6 is a representation of an embodiment of a multi-dose blister pack that may be used in accordance with the principles of this disclosure.

Consider an illustrative example of determining a volume-based fill pattern. FIG. 6 depicts one embodiment of a multi-dose medicament container 10 that may be filled in accordance with the volume-based fill pattern. This embodiment is also disclosed in U.S. Provisional Patent Application Ser. No. 60/940,790 entitled "Multi-Dose Filling Machine and Process" and U.S. Provisional Patent Application Ser. No. 60/947,169 entitled "Nested Multi-Dose Blister Pack." The multi-dose medicament container 10 generally includes a multi-dose blister pack 12 and a cover 14, connected by a spine 16. In one embodiment, the multi-dose blister pack 12 is adapted to contain products such as prescription drugs, for example, for storage and ingestion by a patient. The cover 14 and spine 16 allow the package 10 to be closed similar to a book and may also contain identification information related to a prescription, the product stored in the multi-dose blister pack 12, and/or the patient. It is noted that numerous alternative designs for the product package exist, such as, for example, a tri-fold design or a wallet style, where the blisters are arranged to nest with one another when the package is folded.

In the disclosed embodiment, the cover 14 includes an inside surface 18 carrying a prescription label 20 and a product information/storage device 22. The prescription label 20 may include, for example, patient and prescription information, card number, order number, and other information. The product information/storage device 22 may include an identification, for example, a product identification number, serial number, order number, a bar code or a radio frequency identification (RFID) tag. The product information/storage device 22 may include information related to the patient's course of treatment regarding the prescription drugs. For example, the information may include a dosage amount, a frequency of a dose, side-effect and overdose warnings, drug indications and interactions, benefits, and any other information related to the drug and the course of treatment. Additionally, the depicted embodiment of the package 10 may include a timer 24 such as an electronic timer or visual indicator for signaling to a patient, for example, when to take his/her medication, or for aiding in compliance with the dosing regime(s). The timer 24 is depicted in phantom in FIG. 6 such that it may be understood that the timer 24 may be retained between multiple plies of the material forming the cover 14 such that a visual indicator such as a blinking light may be disposed on an outside surface of the cover 14. In another embodiment, the timer 24 may include an audible indicator such as a speaker for emitting a beep, for example, or a physical indicator such as a vibrating device. Although not depicted, it should be appreciated that alternative embodiments of the package 10 may include either or both of the prescription label 20 and the product information/storage device 22 on an outside surface of the cover 14. So configured, such information may be readily attainable without having to open the cover 14.

The multi-dose blister pack 12 of the package 10 depicted in FIG. 6 includes a plurality of blisters 26 arranged in a matrix 28. Additionally, the multi-dose blister pack 12 includes a removable foil-backing material (not shown) on the backside of the blister pack 12 to seal the blisters 26. The matrix 28 of the embodiment depicted in FIG. 6 includes a four-by-seven matrix, signifying the seven days of the week and the four general times of the day. More particularly, the matrix 28 includes seven rows 30a-30g, each row assigned to one day of the week, i.e., "Sunday," "Monday," "Tuesday," "Wednesday," "Thursday," "Friday," and "Saturday." Additionally, the matrix 28 includes four columns 32a-32d, each column assigned to a distinct time of the day, i.e., "AM," "Noon," "PM," and "Night."

Accordingly, the multi-dose blister pack 12 of FIG. 6 includes twenty-eight blisters 26, each containing a specified dose of one or more drugs for ingestion on that particular day, at that particular time. For example, as depicted, the blister 26 located at row 30a and column 32d, which corresponds to "Sunday," "Night," includes a single tablet 34. Thus, the patient that has been prescribed the multi-dose blister pack 12 knows to ingest tablet 34 during the "Night" on "Sunday." In contrast, blister 26 located at row 30a and column 32c, which corresponds to "Sunday," "PM," includes one tablet 34 and one tablet 36. Accordingly, the patient knows to ingest tablet 34 and tablet 36 in the "PM" on "Sunday." The multi-dose blister pack 12 depicted in FIG. 6 is only one example of how various drugs may be stored for a particular patient. It should be appreciated that the blisters 26 of the multi-dose blister pack 12 may contain generally any number of tablets for ingestion by the particular patient, in accordance with generally any prescription(s). The only limitation on the number of tablets or variations of prescriptions stored by the multi-dose blister pack 12 is the size of the individual blisters 26. Nevertheless, it is foreseeable that the principles of the present disclosure may be applied to multi-dose blister packs having blisters of generally any size and configuration.

Additionally, in the embodiment depicted in FIG. 6, the multi-dose medicament container 10 is designed to contain one or more prescriptions for a single week, i.e., seven days. Thus, a patient with a prescription that lasts more than a week may require multiple product packages, where each package 10 is assigned to a particular week.

With continued reference to FIG. 6, the multi-dose blister pack 12 includes a plurality of cells 38 that constitute the rows 30a-30g and columns 32a-32d of the matrix 28. Thus, each cell 38 accommodates a single blister 26. Additionally, in the disclosed embodiment, each of the cells 38 may be separated by perforated seams 40. So configured, a patient may remove one or more of the cells 38 including the cells' 38 respective blisters 26 from the multi-dose blister pack 12. This allows the patient to discard empty blisters 26 and/or to transport one or more blisters 26 without having to transport the entire package 10. Alternative embodiments may have perforated seams 40 with multiple orientations, or may not include perforated seams 40.

Additionally, as depicted in FIG. 6, each cell 38 includes indicia 42 indicating to the patient when to ingest the tablets stored in the particular blister 26. For example, the blister 26 located at row 30a and column 32d includes indicia 42 identifying "SUN" for Sunday at the left portion of row 30a, and "Night" for night-time at the top portion of column 32d. The remaining cells 38 have similar indicia for different days of the week and times of the day. Additional indicia 42a may include a label for the pack on the side identifying the pack itself. In this example, indicia 42a identifies the pack as containing tablets for the week of Mar. 2-8, 2008. Accordingly, in one embodiment of the present disclosure, while the multi-dose blister pack 12 is unique for every patient, there may be many similarities from one patient's multi-dose blister pack to the next. So configured, not necessarily every blister 26 must be filled for a specific prescription to be satisfied. For example, for a 6-day prescription that begins on Monday and ends on Saturday, the multi-dose blister pack 12 would not include tablets stored in the blisters 26 for Sunday. For a 7-day prescription that begins on Monday and ends on Sunday, a patient may be given two packages 10. The multi-dose blister pack 12 of the first package 10 would include tablets in the blisters 26 only for Monday through Saturday, while the multi-dose blister pack 12 of the second package 10 would only include tablets in the blisters for Sunday, for example. Alternatively, in the example of the 7-day prescription that begins on Monday and ends on Sunday, a patient may be given a single package 10 with customization, such as blister sizes and/or printing to accommodate the dosing regime.

Thus, the patient participating in a dosing regime that includes the multi-dose medicament container 12 of FIG. 6 knows to ingest both tablet 34 and tablet 36 in the morning and evening each day of the week that they are to ingest the medicament(s), and to ingest tablet 34 at noon and at night. Accordingly, in the disclosed embodiment, each of the containers 26 labeled "AM" and "PM" of the multi-dose card 12 contains two tablets, one of medication 34 and one of medication 36. Each of the containers 26 labeled "NOON" and "NIGHT" of the multi-dose card 12 contains one tablet, one of medication 24. Further still, in the embodiment of the multi-dose medicament container 10 disclosed in FIG. 6, the multi-dose card 12 includes a header or dosing regime 42 that is visible when the cover 14 is opened. The dosing regime period 42 of the disclosed embodiment may include indicia of a time of day (e.g., Morning, Afternoon, Evening, Night, AM, PM, Afternoon, Lunch, Dinner, Bedtime, etc.) or other period (daily, every other day, weekly, etc.) information.

However, an alternative embodiment of the package 10 may include a customized multi-dose blister pack 12 for each patient. For example, for a patient receiving a 7-day prescription that begins on Tuesday, for example, the indicia of the dosing regime 42 on the multi-dose blister pack 12 may be printed specifically for that prescription. Thus, each cell 38 in the first row, which is identified by reference numeral 30a in FIG. 6, may be printed with indicia identifying Tuesday. Similarly, the second row 30b would include indicia identifying Wednesday, the third row 30c including indicia identifying Thursday, etc. The same type of customized indicia could also be applied to the specific times of the day that the particular drugs are to be taken. For example, if a certain medication must be taken "With Breakfast," for example, the cells 38 in column 32a may include indicia of the dosing regime 42 reflecting such a prescription. In at least one embodiment, the customized indicia may include a compliance code 44. The compliance code 44 may be associated with any subset of the blisters 26.

Package 10, however, is not limited to the embodiment illustrated by FIG. 6. Other embodiments of package 10 may be used in accordance with the present application. For instance, an embodiment of package 10 may have a multi-dose blister pack 12 for a single time of day indicated by indicia 42a, such as "MORNING." Each blister 26 therein may then be labeled by day and/or week indicia 42, so that each morning, the patient may take package 10 and ingest the medication contained in the blister 26 corresponding to that date's or the day and/or week's indicia 42. In addition to package 10 labeled as "MORNING" by indicia 42a, the patient may have other packages labeled with other times of day by indicia 42a, such as "NOON," "EVENING," "NIGHT," etc. One of ordinary skill in the art will understand that the location of indicia 42a need not be located along the side of medicament container 12 as in FIG. 6, but may be located anywhere on medicament container 12.

Yet another embodiment may have a pack 10 indicated by indicia 42a for a specific month (e.g., "FEBRUARY") and may contain a multi-dose blister pack 12 having a blister 26 containing medication for each day of the month. Each blister 26 may be have indicia 42 indicating the day of the month, e.g., "15," "Feb. 15," "2/15" or the like. One skilled in the art will note that as the configuration of a package 10 may vary, the total number of blisters per multi-dose blister pack 12 may also vary based upon the embodiment or selection by a patient, pharmaceutical professional and/or filling entity. A specific embodiment may be selected based upon patient preference, minimizing the amount of packaging, text translation and/or other criteria. An embodiment may be based upon an indicated number of multi-dose filled blisters on a pack, for instance, if an indication is received or stored corresponding to co-locating two or more blisters containing pills for "Morning" on the same weekly pack. Embodiments of packs 10 are not limited to the embodiments described herein; the present application operates in accordance with any embodiment of a pack 10 containing a multi-dose blister pack 12.

Figure 7:
FIG. 7 illustrates two sample prescriptions for a patient that are used in the subsequent section to illustrate an embodiment of this disclosure.
Figure 7:

FIG. 7 illustrates an example of two sample prescriptions for a patient named Chris Smith 702: a prescription for pill A 704 and a prescription for pill B 706. According to the prescription for pill A 704, pill A is prescribed to be ingested four times per day 708. According to the prescription for pill B 706, pill B is prescribed to be ingested twice a day 710. The information from prescriptions 704, 706 may be collected and sent to the system of FIG. 1 as represented by structures 105 and 145, and/or the method of FIG. 3 as described in blocks 310 and 315.

Consider a first scenario where the one or more prescriptions 704, 706 are to be filled for Chris Smith 702 with a volume-based fill pattern using cuboid volume, as in method 400. Assume the desired multi-dose medicament container is the multi-dose blister pack 12 (MDBP) illustrated in FIG. 6, and the sum of the cuboid volume (SCV) of one pill A and one pill B is less than the cuboid volume of an individual blister cell 26, and that each pack 12 has an indicated number of all multi-dose blister(s) to be filled on the pack. Assume also that the available space for label printing on the backing of an individual blister cell may accommodate the labeling information for four different medications. With these assumptions, the total number of multi-dose blister packs by volume (TNPV) as determined by block 425 of FIG. 4 may be:

TNPV=round (SCV/cuboid volume of an individual blister cell)=1

The total number of multi-dose blister packs by print space (TNPP) may be determined at block 430 as:

TNPP=round (2 pill identifications for same dosing regime/max # of 4 pill identifications able to be printed per blister cell )=1

Therefore, the total number of multi-dose blister packs to fill the prescriptions as determined at block 432 may be:

max (TNPV, TNPP)=max (1, 1)=1 multi-dose blister pack

Although this example illustrates the rounding function as rounding up to the nearest whole number for TNPV and TNPP, the rounding function in other embodiments may use rounding down or other types of rounding in accordance with the present disclosure.

The determined fill pattern that may be communicated to the filling entity for this first scenario is the configuration illustrated in FIG. 6, where pill A may be represented by reference 34 and pill B may be represented by reference 36. The columns corresponding to the AM (references 30a-30g) and PM dosing regimes may contain blister cells filled with both pill A 34 and pill B 36, and the NOON and NIGHT columns may contain blister cells filled with only pill A 34.

Next, consider a second scenario, with the same assumptions as the first scenario except that the sum of the cuboid volumes for pill A 34 and pill B 36 is slightly greater than the cuboid volume of an individual blister cell 26. Again following method 400, the resultant exemplary TNPV as determined by block 425 of FIG. 4 may be:

TNPV=round (SCV/cuboid volume of an individual blister cell )=2

The TNPP as determined by block 430 may be the same as in the first scenario, TNPP=1 Thus, at block 432:

max (TNPV, TNPP)=max (2, 1)=2 multi-dose blister packs

The determined fill pattern that may be communicated to the filling entity for this second scenario would thus result in two MDBPs to fill these prescriptions. One pack may be mapped to contain one pill A in each blister cell. A second pack may be mapped to contain one pill B in the AM and PM columns.

In a third scenario, assume that the desired multi-dose medicament container is the multi-dose blister pack 12 illustrated in FIG. 6, and the sum of the cuboid volume of pills A and B is less than the cuboid volume of an individual blister cell 26. For this third scenario, however, assume that the available space for label printing on the backing of an individual blister cell may accommodate only one medication. Thus, TNPV=1 and TNPP=round (2 pill identifications for same dosing regime/max # of 1 pill identification printed per blister cell )=2

Thus, at block 432:

max (TNPV, TNPP)=max (1, 2)=2 MDBP and the determined fill pattern would be equivalent to the determined fill pattern of the second scenario, albeit obtained by a different path of calculations.

Consider a fourth scenario, this time with an additional pill C (not pictured) prescribed for patient Chris Smith 702 that is to be ingested in the AM and PM along with pills A and B. Assume a selection of a multi-dose blister pack (MDBP), but in this fourth scenario, determining the volume-based fill pattern uses a packing parameter as in method 500, for example, in the case when pill C requires a fixed air cushion, or in the case of other reasons. Assume the packing parameter is a target fill percentage of 50%, and that the printing space on the backing of an individual blister cell may accommodate four medications' worth of information. Again, assume that each pack has an indicated number of all multi-dose blisters to be filled for the pack. Following method 500, assume in this fourth scenario that at block 505, the sum of the pill volume (SPV) for one each of pills A, B and C is determined to be six units, and the volume of an individual blister cell is ten units. At block 510, the target fill volume (TFV) may be determined as:

TFV=50% of individual blister cell volume=50% of 10 units=5 units

At block 512, the maximum number of multi-dose blister packs by volume may be:

TNPV=round (SPV/TFV)=round (6/5)=2

At block 515, the total number of multi-dose blister packs by prescription may be:

TNPP=round (3 pill identifications to be packaged together/max 4 pill identifications able to be printed per blister cell)=1

Thus, at block 520:

max (TNPV, TNPP)=max (2, 1)=2 multi-dose blister packs

The fill pattern is determined to require two multi-dose blister packs to fill the prescriptions for pills A, B and C. The determined fill pattern may then be communicated to the filling entity.

The aforementioned scenarios are exemplary and not intended to cover the complete set of fill pattern possibilities. One skilled in the art will understand that an embodiment of the disclosed methods may operate, for instance, in accordance with a prescription for a medication whose dosing regime requires more than one unit or tablet to be taken at a given time. One of ordinary skill in the art may easily apply the aforementioned system and methods to multiple varieties of scenarios to easily and automatically determine a volume-based filling pattern.

Although the forgoing text sets forth a detailed description of numerous different embodiments, it should be understood that the scope of the patent is defined by the words of the claims set forth at the end of this patent. The detailed description is to be construed as exemplary only and does not describe every possible embodiment because describing every possible embodiment would be impractical, if not impossible. Numerous alternative embodiments could be implemented, using either current technology or technology developed after the filing date of this patent, which would still fall within the scope of the claims.

Thus, many modifications and variations may be made in the techniques and structures described and illustrated herein without departing from the spirit and scope of the present claims. Accordingly, it should be understood that the methods and apparatus described herein are illustrative only and are not limiting upon the scope of the claims.

What is claimed:

1. A method for determining and communicating a volume-based fill pattern of at least one multi-dose medicament container, comprising:
   obtaining a first pill instruction for a first pill for patient, including a first pill identification and a first dosing regime;
   obtaining a second pill instruction for a second pill for the patient, including a second pill identification and a second dosing regime, the first and the second dosing regimes intersecting so that the first and the second pill may be packaged together based on at least a portion of the intersection;
   obtaining pill data for the first and the second pills and container data for the at least one multi-dose medicament container, the pill data including a physical dimension of the first pill and a physical dimension of the second pill;
   determining the volume-based fill pattern using the pill data and the container data by selecting one from a group of volume-based fill pattern types, the group of volume-based fill pattern types including:
      a cuboid volume-based fill pattern, where each receptacle of each at least one multi-dose medicament container is limited to a maximum quantity of pills with a total cuboid volume less than a cuboid volume of the each receptacle, the total cuboid volume of the maximum quantity of pills determined based on the pill data, and
      a volume packing parameter volume-based fill pattern, where the each receptacle of the each at least one multi-dose medicament container is limited to a maximum quantity of pills with a total pill volume less than a target fill volume of the each receptacle, the target fill volume based on a volume packing parameter, the total pill volume of the maximum quantity of pills determined based on the pill data;
   the volume-based fill pattern including a number of at least one multi-dose medicament containers required to hold a set of first and second pills indicated by the first and the second dosing regimes, wherein at least one first pill and at least one second pill are mapped for distribution into a same receptacle of the at least one multi-dose medicament container; and
   communicating the volume-based fill pattern to a filling entity.

2. The method of claim 1, further comprising selecting at least one of:
   a type of the at least one multi-dose medicament container from a group of multi-dose medicament container types including a blister pack, a pouch and a lidded container,
   a size of the at least one multi-dose medicament container, or
   a size of a receptacle of the at least one multi-dose medicament container.

3. The method of claim 1, further comprising determining the volume-based fill pattern using patient input.

4. The method of claim 1, wherein the volume packing parameter comprises a target fill percentage, and the method further comprising selecting the volume packing parameter.

5. The method of claim 1, wherein the first pill is one of a first prescribed medication, a first nutraceutical or a first over-the-counter medication, and wherein the second pill is one of a second medication, a second nutraceutical or a second over-the-counter medication.

6. A method for determining and communicating a fill pattern for at least one multi-dose medicament container, comprising:
   obtaining a first pill instruction for a first pill for patient, including a first pill identification and a first dosing regime;
   obtaining a second pill instruction for a second pill for the patient, including a second pill identification and a second dosing regime, the first and the second dosing regimes intersecting so that the first and the second pill may be packaged together based on at least a portion of the intersection;
   obtaining at least one non-volume fill factor, the at least one non-volume fill factor selected from a group of non-volume fill factors including a drug interaction fill factor and a user selection fill factor;
   selecting the at least one multi-dose medicament container based on the obtained at least one non-volume fill factor;
   obtaining pill data for the first and the second pills and container data for the selected at least one multi-dose medicament container, the pill data including a physical dimension of the first pill and a physical dimension of the second pill;
   determining a volume-based fill pattern using the pill data, the at least one non-volume fill factor and the container data by selecting one from a group of volume-based fill pattern types, the group of volume-based fill pattern types including:
      a cuboid volume-based fill pattern, where each receptacle of each selected at least one multi-dose medicament container is limited to a maximum quantity of pills with a total cuboid volume less than a cuboid volume of the each receptacle, the total cuboid volume of the maximum quantity of pills determined based on the pill data, and
      a volume packing parameter volume-based fill pattern, where the each receptacle of the each selected at least one multi-dose medicament container is limited to a maximum quantity of pills with a total pill volume less than a target fill volume of the each receptacle, the target fill volume based on a volume packing parameter, the total pill volume of the maximum quantity of pills determined based on the pill data;
   the volume-based fill pattern including a number of selected at least one multi-dose medicament containers required to hold a set of first and second pills indicated by the first and the second dosing regimes, wherein at least one first pill and at least one second pill are mapped for distribution into a same receptacle of the selected at least one multi-dose medicament container; and communicating the volume-based fill pattern to a filling entity.

7. The method of claim 6, wherein the drug interaction fill factor comprises at least one from a group of drug interaction fill factors including: an indication of a chemical interaction between the first and the second pills and an indication of a physical interaction between the first and the second pills.

8. The method of claim 6, wherein the user selection fill factor comprises an indication of a user preference for at least one of: a type of the at least one multi-dose medicament container, a size of the at least one multi-dose medicament container, a size of the same receptacle of the selected at least one multi-dose medicament container, or a combination of a number of first pills and a number of second pills to be packaged into the same receptacle of the at least one multi-dose medicament container.

9. The method of claim 6, wherein the volume packing parameter comprises a target fill percentage, and the method further comprising selecting the volume packing parameter.

10. The method of claim 6, wherein the first pill is one of a first prescribed medication, a first nutraceutical or a first over-the-counter medication, and wherein the second pill is one of a second medication, a second nutraceutical or a second over-the-counter medication.

* * * * *